United States Patent [19]

Arneklev et al.

[11] 4,143,069

[45] * Mar. 6, 1979

[54] N-(1,1 SUBSTITUTED PROPYNYL)-α-(3,5-SUBSTITUTED PHENOXY) ALKYL AMIDES

[75] Inventors: Duane R. Arneklev, Sunnyvale; Don R. Baker, Orinda; Francis H. Walker, Mill Valey, all of Calif.

[73] Assignee: Stauffer Chemical Company, Westport, Conn.

[*] Notice: The portion of the term of this patent subsequent to Sep. 27, 1994, has been disclaimed.

[21] Appl. No.: 782,218

[22] Filed: Mar. 28, 1977

Related U.S. Application Data

[63] Continuation of Ser. No. 617,454, Sep. 29, 1975, Pat. No. 4,051,184, which is a continuation of Ser. No. 464,715, Apr. 26, 1974, abandoned, which is a continuation of Ser. No. 353,871, Apr. 23, 1973, abandoned, which is a continuation of Ser. No. 157,058, Jun. 25, 1971, abandoned.

[51] Int. Cl.² ......................................... C07C 103/178
[52] U.S. Cl. ................................................ 260/559 B
[58] Field of Search ...................... 260/559 B; 71/118

[56] References Cited

U.S. PATENT DOCUMENTS

| 2,341,868 | 2/1944 | Hitchcock et al. | 71/118 |
| 2,412,510 | 12/1946 | Jones | 71/118 |
| 3,168,561 | 2/1965 | Richter | 71/118 |
| 3,272,844 | 9/1966 | Easton et al. | 71/118 |
| 3,439,018 | 4/1969 | Brookes et al. | 71/118 |
| 3,534,098 | 10/1970 | Horrom et al. | 72/118 |
| 3,551,484 | 12/1970 | Lewis et al. | 71/118 |
| 3,877,925 | 4/1975 | Cahoy | 71/118 |
| 4,051,184 | 9/1977 | Arneklev et al. | 71/77 |

Primary Examiner—Glennon H. Hollrah
Attorney, Agent, or Firm—Edwin H. Baker

[57] ABSTRACT

N-(1,1 substituted propynyl)-α-(3,5-substituted phenoxy) alkyl amides compounds having the formula

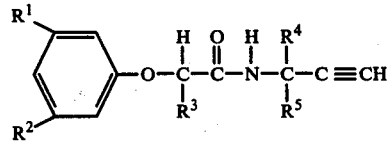

in which $R^1$ and $R^2$ are independently halogen or alkyl having 1 to 4 carbon atoms; $R^3$ is alkyl having 1 to 4 carbon atoms; $R^4$ and $R^5$ are independently hydrogen or alkyl having 1 to 3 carbon atoms; and their use as herbicides.

6 Claims, No Drawings

N-(1,1 SUBSTITUTED PROPYNYL)α(3,5-SUBSTITUTED PHENOXY) ALKYL AMIDES

This is a continuation, of application Ser. No. 617,454, filed Sept. 29, 1975 now U.S. Pat. No. 4,051,184, which is a continuation of application Ser. No. 464,715, filed Apr. 26, 1974 now abandoned, which is a continuation of application Ser. No. 353,871, filed Apr. 23, 1973 now abandoned, which is a continuation of application Ser. No. 157,058, filed June 25, 1971 now abandoned.

This invention relates to certain novel N-(1,1 substituted propynyl)-α-(3,5-substituted phenoxy) alkyl amides which are useful as herbicides.

The compounds of the present invention are new compositions of matter and correspond to the formula

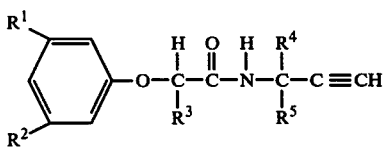

in which $R^1$ and $R^2$ are independently halogen, preferably chlorine or alkyl having 1 to 4 carbon atoms, preferably methyl; $R^3$ is alkyl having 1 to 4 carbon atoms, preferably ethyl; $R^4$ and $R^5$ are independently hydrogen or alkyl having 1 to 3 carbon atoms, preferably methyl, more preferably both $R^4$ and $R^5$ are methyl.

In the above description of the compounds of this invention, alkyl includes both straight chain and branched chain configurations, for example, methyl, ethyl, n-propyl, isopropyl, n-butyl, sec-butyl or tert.-butyl. The term halogen includes chlorine, bromine, iodine and fluorine.

The closest prior art known to applicants in U.S. Pat. No. 3,272,844.

The compounds of this invention are active herbicides of a general type. That is, they are herbicidally effective against a wide range of plant species. The method of controlling undesired vegetation of the present invention comprises applying an herbicidally effective amount of the above-described compounds to the area where control is desired.

An herbicide is used herein to mean a compound which controls or modifies the growth of plants. By a "growth controlling amount" is meant an amount of compound which causes a modifying effect upon the growth of plants. Such modifying effects include all deviations from natural development, for example, killing, retardation, defoliation, dessication, regulation, stunting, tillering, stimulation, dwarfing and the like. By "plants" it is meant germinating seeds, emerging seedlings, and established vegetation including the roots and above-ground portions.

The compounds of the present invention are prepared by the following general method.

Reaction No. 1

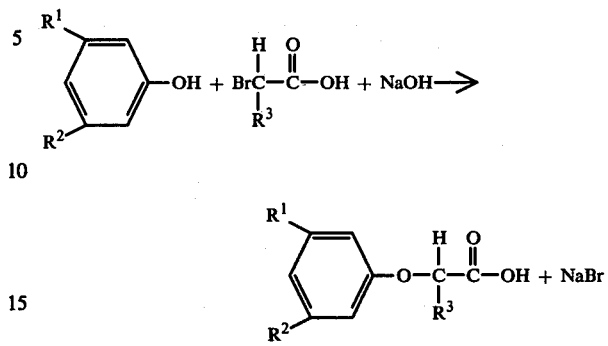

Generally, a mole amount of the phenol, a slight mole excess of the α-bromoalkanoic acid and about 3 moles of sodium hydroxide are mixed in water at about 10° C.–15° C. Then the reaction mixture is heated at reflux for about 2 hours. Thereafter the mixture is cooled and diluted with water. The pH of the mixture is adjusted to 8 with 19% hydrochloric acid. The solution is extracted several times with ether followed by a pH adjustment to 2 with 19% HCl. An oil separates which is extracted with ether.

Evaporation of the ether after drying yields the desired product which is a solid. The solid is purified by recrystalization with cyclohexane.

Reaction No. 2

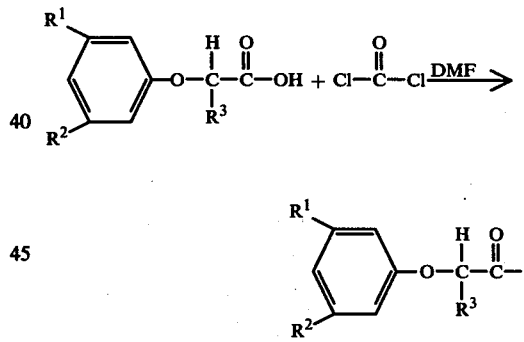

First the acid is mixed in benzene. A small amount of the dimethyl formamide is added and the slurry is heated. A slight excess of the phosgene reactant is added to the acid mixture in portions. The reaction is complete upon termination of HCl evolution. Evaporation of the reaction mixture yields the desired product, a liquid.

Reaction No. 3

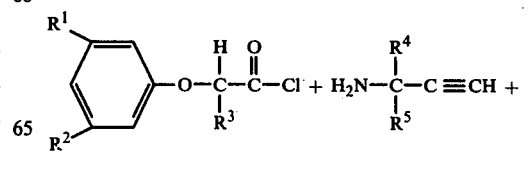

$(C_2H_5)_3N \longrightarrow$

-continued

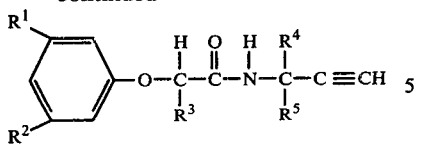

About equal mole amounts of the amines are dissolved in benzene. The solution is cooled to about 10° C. About an equal mole amount of the acid chloride reactant is slowly added to the amine solution at a rate to maintain the temperature between 10°-15° C. After the acid chloride addition is complete, the mixture is heated to 45°-50° C. for 1 hour and then is cooled to room temperature. The mixture is diluted with H$_2$O to dissolve the amine hydrochloride. Some solid remains undissolved and this is filtered. The filtrate is washed two times with 10% HCl With each wash more solid separates and it is filtered. The organic layer is next washed two times with 5% Na$_2$CO$_3$ and dried over Mg SO$_4$. Removal of solvent leaves a solid product which is combined with the solid product previously removed.

Preparation of the compounds of this invention is illustrated by the following reaction.

EXAMPLE

Preparation of N-(1,1 dimethyl propargyl)-α-(3,5-dichlorophenoxy) butyramide

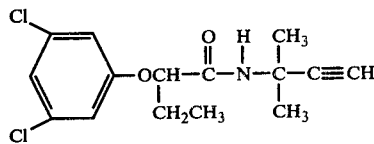

100.0 g. (0.614 moles) of 3,5-dichlorphenol and 112.5 g. (0.675 moles) of α-Bromobutyric acid are mixed and 100 ml. of water is added. The mixture is cooled to 10° C. in an ice water bath and 147.2 g (1.842 moles) 50% NaOH is added dropwise over 10°-15° C. The reaction mixture is warmed to room temperature and then heated at reflux for two hours. After cooling, the mixture is diluted with H$_2$O to 600 ml. and the pH is adjusted to 8 with 19% HCl. The aqueous solution is extracted 3 times with 150 ml. portions of ether and is then adjusted to pH 2 with 19% HCl. An oil separates which is extracted with ether. Evaporation of the ether after drying leaves a white solid, 94.3 g., m.p. 102°-108° C. This solid is recrystalized from 250 ml. cyclohexane to give 71.8 g. α-(3,5-dichlorophenoxy) butyric acid m.p. 113°-116° C.

71.8 g. (0.288 moles) of α-(3,5-dichlorophenoxy) butyric acid and 75 ml. of benzene are placed in a 500 ml. flask to which a dropping funnel with dry-ice condenser is attached. The slurry is stirred and the 0.2 ml. dimethyl formamide is added. The mixture is heated to 35° C. and 10 g. of phosgene is condensed into the mixture to initiate reaction. The start of the reaction is evidenced by HCl evolution and foaming. 26.0 g. more phosgene is added in 5 gm. increments. At the conclusion of the reaction (HCl evolution ceasing), the reaction mixture is evaporated leaving a residual liquid α-(3,5-dichlorophenoxy) butyryl chloride 77.6 g., N$_D^{20}$ = 1.5345

164 g. (1.63 moles) triethyl amine and 132 g. (1.58 moles) 3-methyl-3-amino-1-butyne are dissolved in 1300 ml. benzene and the solution is cooled to 10° C. in an ice water bath.

412.9 g. (1.55 moles) α-(3,5-dichlorophenoxy) butyryl chloride diluted with 200 ml. benzene is added dropwise to the amine solution. Periodic additions of benzene (400 ml.) are made in order to adequately stir the mixture. After acid chloride addition is complete, the mixture is heated to 45°-50° C. for 1 hour more and then allowed to come to room temperature overnight. The mixture is diluted with 1000 ml. H$_2$O to dissolve the amine hydrochloride. Some solid remains undissolved and this is filtered. The filtrate is washed two times with 1000 ml. 10% HCl. With each wash more solid separates and it is filtered. The organic layer is next washed two times with 5% Na$_2$CO$_3$ and dried over Mg SO. Removal of solvent leaves 377 g. which is combined with the previously removed solid to yield 436 g. of the desired product, m.p. 90°-94° C.

The following is a table of certain selected compounds that are preparable according to the procedure described hereto. Compound numbers are assigned to each compound and are used through the remainder of the application.

Table I

| Compound Number | R$^1$ | R$^2$ | R$^3$ | R$^4$ | R$^5$ |
|---|---|---|---|---|---|
| 1 | CH$_3$ | CH$_3$ | CH$_3$ | CH$_3$ | CH$_3$ |
| 2 a) | Cl | Cl | CH$_3$CH$_2$ | CH$_3$ | CH$_3$ |
| 3 | CH$_3$ | CH$_3$ | CH$_3$CH$_2$ | CH$_3$ | CH$_3$ |
| 4 | Cl | Cl | CH(CH$_3$)$_2$ | CH$_3$ | CH$_3$ |
| 5 | Cl | Cl | CH$_3$CH$_2$CH$_2$ | CH$_3$ | CH$_3$ |
| 6 | Cl | Cl | CH$_3$CH$_2$ | H | H |
| 7 | CH$_3$ | CH$_3$ | CH$_3$CH$_2$ | H | H | a) Prepared in Example 1.

Herbicidal Screening Tests

As previously mentioned, the herein described compounds produced in the above-described manner are phytotoxic compounds which are useful and valuable in controlling various plant species. Selected compounds of this invention are tested as herbicides in the following manner.

Pre-emergence herbicide test. On the day preceding treatment, seeds of seven different weed species are planted in individual rows using one species per row across the width of the flat. The seeds used are hairy crabgrass (*Digitaris sanguinalis* (L.) Scop.), yellow foxtail (*Setaria glauca* (L.) Beauv.), watergrass *Echinochloa crusgalli* (L.) Beauv.), California red oat (*Auena sativa* (L.), redroot pigweed (*Amaranthus retroflexs* (L.) Indian mustard (*Brassica juncea* (L.) Coss.) and curly dock (*Rumex crispus* (L.). Ample seeds are planted to give about 20 to 50 seedlings per row, after emergence, depending upon the size of the plants. The flats are watered after planting. The spraying solution is prepared by dissolving 50 mg. of the test compound in 3 ml. of a solvent, such as acetone, containing 1% Tween 20 ® (polyoxyethylene sorbitan monolaurate). The following day each flat is sprayed at the rate of 20 pounds of the candidate compound per 80 gallons of solution per acre. An atomizer is used to spray the solution onto the soil surface. The flats are placed in a greenhouse at 80° F. and watered regularly. Two weeks later the degree of weed control is determined by comparing the amount of germination and growth of each weed in the treated flats with the same weeds in several untreated control flats. The rating system is as follows:

- − = no significant injury (0-15 percent control)
- + = slight injury (25-35 percent control)
- + + = moderate injury (55-65 percent control)
- + + + = severe injury or death (85-100 percent control)

An activity index is used to represent the total activity of all seven weed species. It is the sum of the number of plus marks, so that an activity index of 21 represents almost complete control of all seven weeds. The results of this test are reported in Table II.

Post-emergence herbicide test. Seeds of five weed species including hairy crabgrass, watergrass, California red oats, Indian mustard, and curly dock and one crop, pinto beans (*Phaseolus vulgaris*), are planted in flats as described above for pre-emergence screening. The flats are placed in the greenhouse at 72°-85° F. and watered daily with a sprinkler. About 10 to 14 days after planting when the primary leaves of the bean plant are almost fully expanded and the first trifoliate leaves are just starting to form, the plants are sprayed. The spray is prepared by weighing out 50 mg. of the test compound, dissolving it in 5 ml. of acetone containing 1% Tween 20 ® (polyoxyethylene sorbitan monolaurate) and then adding 5 ml. of water. The solution is sprayed on the foliage using an atomizer. The spray concentration is 0.5% and the rate would be approximately 20 pounds per acre if all of the spray was retained on the plant and the soil, but some spray is lost so it is estimated that the application rate is approximately 12.5 pounds per acre.

Beans are used to detect defoliants and plant growth regulators. The beans are trimmed to two or three plants per flat by cutting off the excess weaker plants several days before treatment. The treated plants are placed back in the greenhouse and care is taken to avoid sprinkling the treated foliage with water for three days after treatment. Water is applied to the soil by means of a slow stream from a watering hose taking care not to wet the foliage.

Injury rates are recorded 14 days after treatment. The rating system is the same as described above for the pre-emergence test where (−), (+), (++), and (+++) are used for the different rates of injury and control. The injury symptoms are also recorded. The maximum activity index for complete control of all the species in the post-emergence screening test is 18 which represents the sum of the plus marks obtained with the six plant species used in the test. The herbicide activity is shown in Table II.

TABLE II
HERBICIDAL ACTIVITY SCREENING RESULTS

| Compound Number | Herbicidal Activity Index** | |
|---|---|---|
| | Pre-emergence (20 lb/A) | Post-emergence (12.5 lb/A) |
| 1 | 21 | 17 |
| 2 | 21 | 15 |
| 3 | 21 | 15 |
| 4 | 12 | 3 |
| 5 | 18 | 13 |
| 6 | 20 | 15 |
| 7 | 21 | 15 |

**21 = 85-100% control of all seven plant species tested pre-emergence.
18 = 85-100% control of all six plant species tested post-emergence.

The compounds of the present invention are used as pre-emergence or post-emergence herbicides and are applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for both pre- and post-emergence herbicidal applications are wettable powders, emulsifiable concentrates and granules. These formulations may contain as little as about 0.5% to as much as about 95% or more by weight of active ingredient. The amount applied depends upon the nature of the seeds or plants to be controlled and the rate of application varies from ⅛ to approximately 50 pounds per acre.

Wettable powders are in the form of finely divided particles which disperse readily in water or other dispersant. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient by weight and usually also contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthas, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations, wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredient and may also contain small amounts of other ingredients which may include surface-active agents such as wetting agents, dispersing agents or emulsifiers; oils such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours, and other organic and inorganic solids which act as dispersants and carriers for the toxicant, are useful formulations for soil-incorporating applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene or other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to convention methods and are distributed in the soil to a depth of at least ½ inch below the soil surface. It is not necessary that the phytotoxic compositions to be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-s-triazine, 2-chloro-4-ethylamino-6-isopropylamino-s-triazine, and 2-ethylamino-4-isopropylamino-6-methylmercapto-s-triazine; urea derivatives, such as 3-(3,4-dichlorophenyl)-1,1-dimethyl urea and 3-(p-chlorophenyl)-1,1-dimethyl urea: and acetamides such as N,N-diallyl-α-chloroacetamide, and the like; benzoic acids such as 3-amino-2,5-dichlorobenzoic; thiocarbamates, such as S-propyl dipropylthiocarbamate, S-ethyldipropylthiocarbamate, S-ethyl cyclohexylethyl thiocarbamate, S-ethyl hexahydro-1H-azepine-1-carbothioate and the like; 4-(methylsulfonyl)-2,6-dinitro-N,N-substituted anilines, such as 4-(methylsulfonyl)-2,6-dinitro-N,N-di-n-propyl aniline, 4-trifluoromethyl-2,6-dinitro-N,N-substituted anilines, such as 4-trifluoromethyl-2,6-dinitro-N,N-di-n-propyl aniline and 4-trifluoromethyl-2,6-dinitro-N-ethyl-N-n-butyl aniline. Fertilizers useful in combination with the active ingredients include, for example, ammonium nitrate, urea and superphosphate. Other useful additaments include materials in which plant organisms take root and grow such as compost, manure, humus, sand and the like.

The concentration of a compound of the present invention, constituting an effective amount of the best mode of administration in the utility disclosed is readily determinable by those skilled in the art.

It is claimed:
1. Compounds of the formula

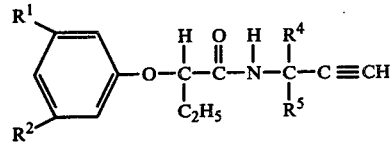

in which $R^1$ and $R^2$ are both chlorine or both methyl; $R^4$ is hydrogen or methyl and $R^5$ is hydrogen, methyl or ethyl provided that $R^4$ and $R^5$ are both not methyl.

2. The compound of claim 1 in which $R^1$ is methyl, $R^2$ is methyl, $R^4$ is hydrogen, and $R^5$ is hydrogen.

3. The compound of claim 1 in which $R^1$ is chlorine, $R^2$ is chlorine, $R^4$ is hydrogen and $R^5$ is hydrogen.

4. The compound of claim 1 in which $R^1$ is methyl, $R^2$ is methyl, $R^4$ is methyl and $R^5$ is hydrogen.

5. The compound of claim 1 in which $R^1$ is chloro, $R^2$ is chloro, $R^4$ is methyl and $R^5$ is ethyl.

6. The compound of claim 1 in which $R^1$ is methyl, $R^2$ is methyl, $R^4$ is methyl and $R^5$ is ethyl.

* * * * *